US011311714B2

(12) United States Patent
Matheis et al.

(10) Patent No.: US 11,311,714 B2
(45) Date of Patent: Apr. 26, 2022

(54) ARRANGEMENT WITH A BLOOD PUMP, A CONTROL UNIT AND A DEVICE FOR TRANSMITTING THE MEASURED VALUES

(71) Applicant: Xenios AG, Heilbronn (DE)

(72) Inventors: Georg Matheis, Heilbronn (DE); Sebastian Koehler, Nordheim (DE)

(73) Assignee: Xenios AG, Heilbronn (DE)

( * ) Notice: Subject to any disclaimer, the term of this patent is extended or adjusted under 35 U.S.C. 154(b) by 112 days.

(21) Appl. No.: 16/482,752

(22) PCT Filed: Feb. 1, 2018

(86) PCT No.: PCT/DE2018/000019
§ 371 (c)(1),
(2) Date: Aug. 1, 2019

(87) PCT Pub. No.: WO2018/141323
PCT Pub. Date: Aug. 9, 2018

(65) Prior Publication Data
US 2020/0000989 A1  Jan. 2, 2020

(30) Foreign Application Priority Data
Feb. 2, 2017  (DE) ...................... 10 2017 000 940.6

(51) Int. Cl.
*A61M 1/10* (2006.01)
*A61M 60/50* (2021.01)
(Continued)

(52) U.S. Cl.
CPC .......... *A61M 60/50* (2021.01); *A61M 60/148* (2021.01); *A61M 60/40* (2021.01);
(Continued)

(58) Field of Classification Search
CPC .......... A61M 60/00; A61M 2205/3365; A61M 2205/3334; A61M 2230/04;
(Continued)

(56) References Cited

U.S. PATENT DOCUMENTS 3,206,768 A    9/1965  Preston
7,988,728 B2*  8/2011  Ayre ................... A61M 60/824
                                                      623/3.28
(Continued)

FOREIGN PATENT DOCUMENTS

CN  101002969 A  7/2007
CN  101663056 A  3/2010
(Continued)

OTHER PUBLICATIONS

International Search Report in PCT/DE2018/000019, dated May 29, 2018.
(Continued)

*Primary Examiner* — Jon Eric C Morales
(74) *Attorney, Agent, or Firm* — Collard & Roe, P.C.

(57) ABSTRACT

An assembly with a blood pump and a control unit to control the flow rate at the blood pump includes a device that is designed to deliver a parameter of the breathing cycle or a parameter associated with the breathing cycle. In this way, it is also made possible for a parameter that correlates to the breathing cycle to be used to control the blood pump, in order to proactively prevent problems associated with the drainage.

16 Claims, 2 Drawing Sheets

Figure 1:
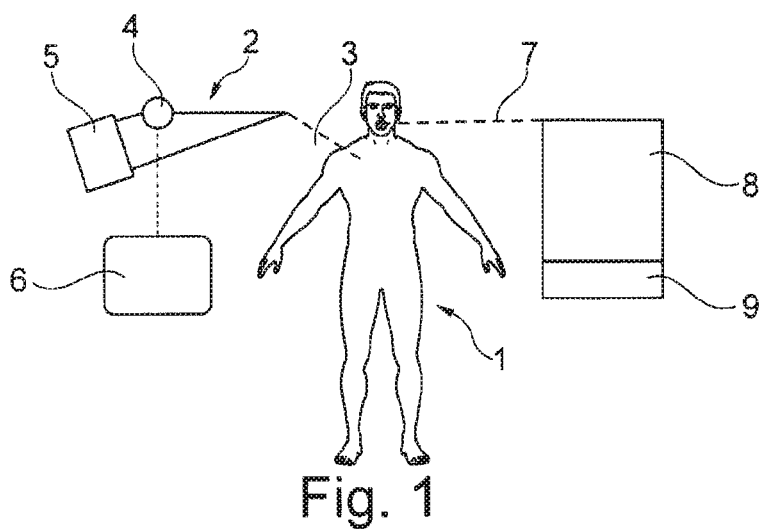

(51) Int. Cl.
    *A61M 60/40*     (2021.01)
    *A61M 60/148*     (2021.01)
    *A61B 5/0215*     (2006.01)

(52) U.S. Cl.
    CPC .... *A61B 5/0215* (2013.01); *A61M 2205/3344* (2013.01); *A61M 2230/04* (2013.01); *A61M 2230/30* (2013.01)

(58) Field of Classification Search
    CPC .......... A61M 2230/06; A61M 2230/63; A61M 60/122; A61M 60/857; A61B 5/024; A61B 5/0809
    See application file for complete search history.

(56) References Cited

U.S. PATENT DOCUMENTS

| | | | |
|---|---|---|---|
| 8,672,868 | B2 | 3/2014 | Simons |
| 2005/0059935 | A1 | 3/2005 | Yamazaki et al. |
| 2007/0112325 | A1* | 5/2007 | Wieselthaler ....... A61M 31/002 604/500 |
| 2007/0129666 | A1 | 6/2007 | Barton et al. |
| 2008/0183287 | A1 | 7/2008 | Ayre |
| 2011/0054239 | A1* | 3/2011 | Sutton ................... A61M 60/50 600/16 |
| 2015/0030502 | A1 | 1/2015 | Gorhan et al. |
| 2017/0087289 | A1* | 3/2017 | Yomtov .............. A61M 60/562 |
| 2017/0095601 | A1 | 4/2017 | Laubscher et al. |

FOREIGN PATENT DOCUMENTS

| | | | |
|---|---|---|---|
| DE | 10 2014 107980 A1 | 12/2015 | |
| EP | 0 000 831 A1 | 2/1979 | |
| EP | 1514571 A2 * | 3/2005 | .......... A61M 1/3661 |
| EP | 2 117 623 B1 | 11/2013 | |
| EP | 2 832 383 A1 | 2/2015 | |
| JP | H04-317659 A | 11/1992 | |
| JP | 2004-313498 A | 11/2004 | |
| JP | 2005-87337 A | 4/2005 | |
| JP | 2009-542391 A | 12/2009 | |
| JP | 2014-512197 A | 5/2014 | |
| JP | 2016-525894 A | 9/2016 | |
| JP | 2016-538898 A | 12/2016 | |
| WO | 2011/021978 A1 | 2/2011 | |
| WO | 2015/185618 A1 | 12/2015 | |
| WO | 2018/073150 A1 | 4/2018 | |

OTHER PUBLICATIONS

Japanese Notice of Reasons for Rejection in Japanese Application No. JP 2019-539198 dated Jan. 4, 2022.

* cited by examiner

ARRANGEMENT WITH A BLOOD PUMP, A CONTROL UNIT AND A DEVICE FOR TRANSMITTING THE MEASURED VALUES

CROSS REFERENCE TO RELATED APPLICATIONS

This application is the National Stage of PCT/DE2018/000019 filed on Feb. 1, 2018, which claims priority under 35 U.S.C. § 119 of German Application No. 10 2017 000 940.6 filed on Feb. 2, 2017, the disclosure of which is incorporated by reference. The international application under PCT article 21(2) was not published in English.

The invention relates to an assembly with a blood pump, a control unit for controlling the flow rate at the blood pump, and at least one device for transmitting the measurement values to the control unit.

During Extracorporal Lung and Heart Assistance (ECLA/ECLS or ECMO, ECCO2R), the target blood flow is dependent on a variety of factors (cannula size, properties of the membrane lung, intravascular blood volume and the ratio between the vascular diameter and the cannula diameter). In this context, it can happen that the openings in the cannula adhere to the vessel wall and are blocked during blood withdrawal or drainage.

In order to supply blood to the body during the above-mentioned procedures, cannulae that guarantee sufficient blood flow are used. Depending on the application, cannulae with an outer diameter of about 12-32 Fr (French) and a length of about 90 to 800 mm are used for this.

With regard to these cannulae, a distinction is made between single lumen and dual lumen cannulae. Examples of these are the NovaPort® twin dual lumen cannula from Novalung® or the Medos® femoral cannula.

During drainage, the cannula is most often advanced as far as the heart and into the vena cava, or even into the right atrium. Typical cannulation sites for drainage are the vena femoralis, vena jugularis or vena subclavia. Consequently, the cannula tip and the drainage area of the cannula is often located in the region of the thorax.

With spontaneous breathing and ventilation, the expansion of the internal volume of the thorax can cause the filling of the blood vessels or the volume of blood in the thoracic vessels and in the periphery to change during the breathing cycle. The cannula is then left dry and adheres to the vessel wall, because at certain phases of the breathing cycle less blood volume is present than patient pressure (patient's blood flow).

During ventilation, the lung is exposed to constant positive pressure during both inspiration and expiration. In contrast, during inspiration in spontaneous breathing the pressure in the lung is occasionally lower than ambient pressure. Thus, a distinction must be made between two different respiration modes.

A species-related assembly for assuring a pulsatile and synchronised return of blood to the patient's heart is described in EP 2 832 383 A1. In this case, a control unit acts on a blood pump and an EKG provides a control signal to the control unit so that the control unit can control the flow rate at the pump according to the EKG values.

EP 2 832 383 A1 thus describes a pump procedure triggered by an EKG, in which blood is pumped back into the patient from an ECLS assembly for example, in a manner suitable for the correct cardiac phase. The pump creates special pulse peaks to support the heart. This creates the problem according to which the volumetric flow required to support the heart must also be withdrawn from the patient and can even lead to volumetric flow spikes at the blood withdrawal cannula. This in turn exacerbates the problem of the cannula adhering to the vessel wall through suction.

This problem can be mitigated by providing the cannula with suitable shaping or with a compensating vessel in the blood circulatory system.

EP 2 117 623 B1 suggests determining values for the blood flow in order to increase the rotating speed of a blood pump stepwise and throttle it shortly before vessel collapse. In this way, blood flow problems can be addressed temporarily.

However, most lung and heart assistance methods use a continuous blood flow. In this, the rotating speed of the blood pump or the target blood flow is set manually to define the blood flow. For example, an ECMO system is monitored by measurement of three pressure measurement points in the extracorporeal circuit or measurement of the pressure differential between the measurement points. This makes it easier to identify the location of the problem in the event of a rise in pressure. Moreover, threshold values at which an alarm is triggered can be set on the control unit.

The problem addressed by the invention is that of enabling a blood flow which is as safe, suitable and gentle as possible. It is further designed to alleviate the problem of the cannula adhering to a vessel wall during constant blood flow and particularly also with changing blood volume flow.

This problem is solved with a species-related assembly in which the device is designed to deliver a parameter of the breathing cycle or a parameter connected to the breathing cycle. In this way, the maximum possible blood flow adapted to the status of the vessel can may be provided.

According to the invention, an intelligent, automated and improved blood pump control is provided, which is triggered by the breathing cycle or a parameter associated therewith. This makes it possible to determine the optimum points in time to increase or reduce the pump output in order to transport the blood volume required for the extracorporeal circuit with low impact on the blood and with the smallest cannula possible.

By this means, it is possible to control the flow rate at the blood pump so that is synchronised with the current patient conditions (i.e. with the filled state of the large veins which varies over the breathing cycle), not only in extreme cases, but continuously to the extent possible, in order to proactively avoid problems related to drainage. In this context, blood flows up to 5 and preferably up to 8 l/min should be achieved without having to worry about the cannula adhering to the vessel wall. With the breathing-triggered drainage, it is possible to wait for the optimum point in time for withdrawing the patient's blood depending on the patient's respiration, and to adjust the blood volume flow accordingly. This enables a gentle blood flow and prevent the cannula from adhering to the vessel wall.

With the assembly according to the invention, the drainage may be improved while the risk of drainage problems is minimised. In this way, the best possible care can be provided for the patient. Since the sensors for determining the parameters already exist, an assembly of such kind is easy to construct and adapt directly for use with a patient. Thus, the suggested solution is a simple but highly effective solution for preventing the cannula from adhering to a vessel wall and enabling a particularly high blood volume flow. This also assures particularly safe treatment of the patient, since a continuous, high blood flow guarantees the effectiveness of gas exchange systems.

The signal input for this triggering can be—but does not have to be—an EKG. In clinical use, it must be noted whether the patient receives artificial, that is to say mechanical ventilation. This is important for determining whether the output of the blood pump, for example a peristaltic pump or an axial, radial or diagonal pump, will be increased or throttled.

A blood pump with a drive of which the output can be controlled to vary the flow rate at the blood pump is suitable as part of the assembly.

It is advantageous if the blood pump has a rotor for controlling the rotating speed thereof in order to vary the flow rate.

It is particularly advantageous if the assembly has a gas exchanger which decarboxylates (removes $CO_2$ from) the patient's blood and if necessary also oxygenates it (enriches with $O_2$).

An advantageous design variant provides that the device is an EKG and the parameter correlates to an impedance of the EKG. An EKG may also be used for a ventilated patient. However, the use of an EKG is particularly advantageous for a spontaneously breathing patient.

In order to be able to identify the corresponding trigger points, the sensor data already used in practice may be utilised. Thus for example the respiratory rate of a spontaneously breathing patient may be transmitted to the control unit via the impedance of the EKG, in particular via the EKG monitoring cable.

Alternatively or in addition thereto, it is suggested that the device is a ventilator and the parameter correlates with an inspiratory pressure of the ventilator. Then the device is prioritised above all other sensor data and used as a trigger signal. The inspiratory pressure is represented as a continuous pressure-time-diagram, the apsides or plateau phases of which are used optionally with a temporal deviation as a trigger signal or trigger point to be to be transmitted to the control unit as parameters. In this way, particularly for ventilated patients the parameters can be controlled by the ventilator.

It is further suggested that the device may be a chest strap. The parameter then correlates to a stretching or tension in the chest strap.

Equally, the device may also be a piezo element.

As a further design variant of the device, a diaphragm sensor or a myocardial sensor is suggested. A myocardial sensor is an EMG sensor (electromyography sensor) which measures electromuscular activity, that is to say the action potential of the muscles. It can be used for example to measure the activity of the respiratory musculature, in order to transmit the measurement values (e.g., peaks) to the control unit as a trigger point.

Additionally, the device may also be a sensory gastric tube which transmits measurement values to the control unit.

It is advantageous if as much sensor data as possible is transmitted to the control unit. This makes it possible to monitor blood flow and gas flow parameters of a gas exchanger and a ventilator with the control unit, and to regulate particularly the ventilator and optionally the temperature control for the gas exchanger as well with the control unit, and to enter at least the significant parameters at the control unit.

Particularly advantageous is a hybrid solution, both for extracorporeal lung or heart assistance and for ventilation of the patient by means of a control unit which is usable for both functions, which automatically controls the blood flow and gas flow parameters for the ventilator and provides parallel intelligent ventilation.

A critically important consideration is whether a patient breathes spontaneously or is ventilated. In the case of spontaneous breathing, the rotating speed should be reduced when breathing in and increased when breathing out. With ventilation, the principle is reversed. With the assembly described, it is possible to distinguish between these two phases and to detect the current situation automatically in order to control the flow rate at the blood pump correspondingly. This is made possible according to the invention by the interfaces provided.

A greater blood withdrawal at a certain time interval of the breathing cycle also results correspondingly in a temporally increased return of blood volume. This can cause problems (e.g., recirculation or shunt) for example when a venovenous cannulation such as a venovenous dual lumen cannula is inserted, because the withdrawal and return take place at sites very close to each other. For this reason, the advantages of the invention are also particularly distinct when the blood is withdrawn from a vein and returned to an artery.

The control unit is able to select or combine measurement values from different devices on the basis of previously entered data to control the flow rate at the blood pump. This makes it possible for the control unit to select signals from various device inputs or to produce a combined trigger signal.

In practice, the control unit as an apparatus is able to detect the signal input of the various "devices" by means of a conducting signal or contact, alternatively also a mechanical connection (simple switch). There are several connection points or sockets in a control unit. In the case of mechanical ventilation, there is necessarily a ventilator and thus also a signal input. The control unit may have a separate socket/port for this, which is only suitable for the ventilator and the corresponding plug, and is also identified as such. If this socket is occupied and the signal is used, the blood pump is operated accordingly with the controller for mechanical ventilation.

In practice, the input signal is "handled" by the control unit with an algorithm. The algorithm polls all signal inputs continuously and checks regularly for faulty signals. A memory is used for this. Here, the required parameters of any input signal and the associated maximum deviations are noted. Additionally, any "noise" in the input signal can be subtracted beforehand with the aid of an additional algorithm or mathematical operation (e.g., Laplace) to avoid inaccuracies.

All tested signals are evaluated and prioritised by the control unit. At least one tested signal (from the "device") must be present. If there are multiple signal inputs, the one that is higher on the list (in the memory) is used/prioritised. Additional signal inputs with the aid of a further memory serve to refine the activation point (signal to the blood pump (exactly when output reduced or increased) by offsetting the values live, in a CPU or a RAM memory for example. Together with further parameters for retardation, it is thus possible to calculate an optimum timing for the blood pump.

Moreover, it is a simple matter for the control unit to calculate automatically (without manual adjustments by the doctor) whether the signal is for a spontaneously breathing or a ventilated patient. For this purpose various parameters (such as pressure) are also compared correspondingly with target values from the memory. See paragraph [07] above.

In order to insert a delay in the circuit in particular for a venovenous cannulation, that is to say in order to return the blood not immediately after withdrawal, it is suggested that a buffer element is arranged after the blood pump. The buffer element may be for example a small, flexible storage space or reservoir. Further options are made available by the use of a double pump variant or a valve-controlled return.

In terms of the method, the problem the invention is designed to address is solved with a method for using an assembly of such kind, in which the measurement values are compared with predefined measurement values by the controller for the purpose of controlling the flow rate of the blood pump and/or the gas flow of a ventilator.

In this context, it is advantageous if spontaneous breathing and ventilation are detected with the controller automatically and the flow rate of the blood pump is controlled accordingly.

Figure 2:
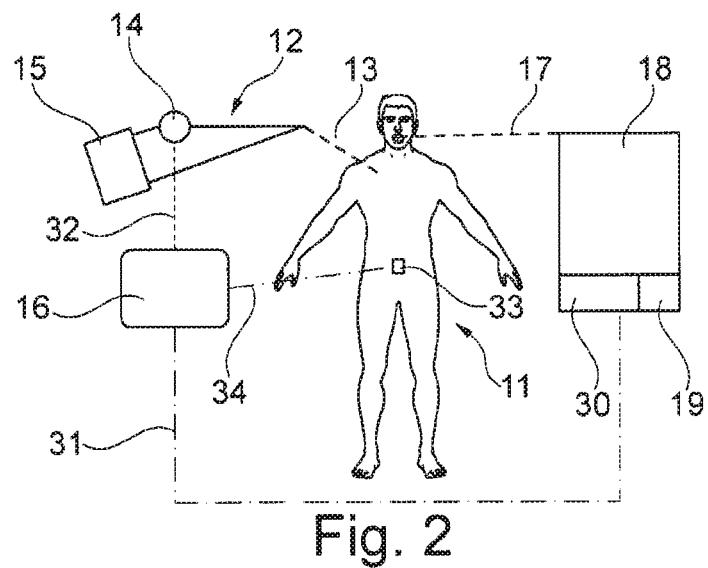
Figure 3:
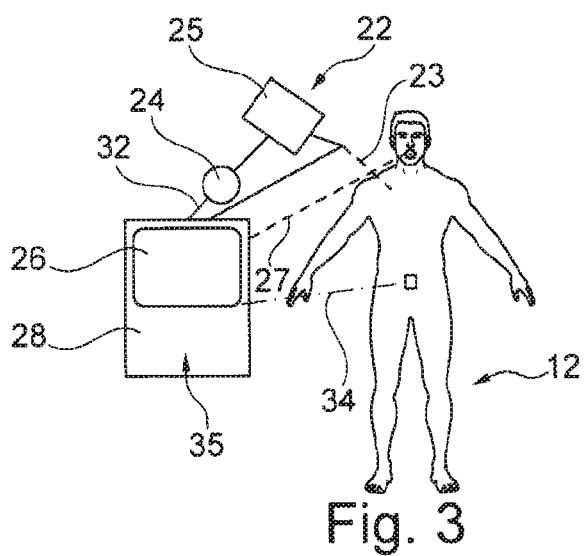
Figure 4:
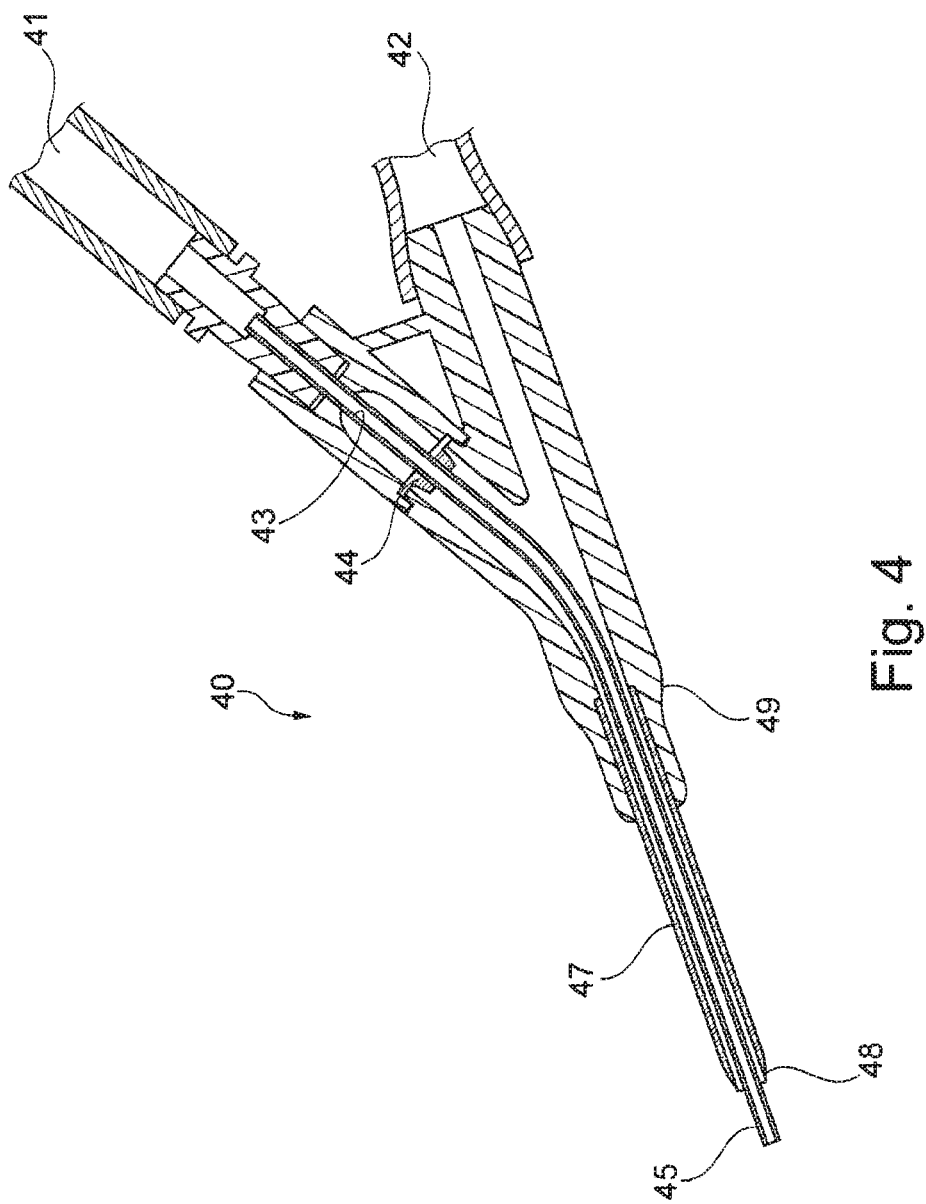

In the following text, the invention will be explained in greater detail with reference to the drawing. In the drawing:

FIG. 1 is a schematic representation of the treatment of a patient in an intensive care unit according to the related art, FIG. 2 is a schematic representation of the treatment of a patient in an intensive care unit with sensor input and interface for ventilation, FIG. 3 is a schematic representation of the treatment of a patient in an intensive care unit with a shared control unit, and FIG. 4 is a schematic representation of a cross section through a dual lumen cannula.

The patient 1 shown in FIG. 1 is connected to an assembly 2 via a cannula 3. The assembly 2 includes a blood pump 4 and a gas exchanger 5. The blood pump 4 is connected to a control unit 6, which controls the flow rate at the blood pump 4. With the cannula 3 in the form of a dual lumen cannula it is possible to withdraw and return blood from and to the same blood vessel. In this process, the construction and assembly of the cannula ensures that the blood which is returned is not immediately withdrawn again. The consequence of this is that the vessel wall may be drawn against the cannula in the blood withdrawal area if the following blood is not able to flow fast enough. This in turn causes the aspiration openings in the cannula to be occluded by the vessel wall and the vessel collapses. The control unit may serve to pump blood back into the patient in synchronisation with the correct cardiac phase. The following description will explain how the control unit makes it possible to wait for the optimum point in time for withdrawing blood from the patient depending on the patient's breathing, and to adjust the blood flow accordingly.

For this reason, the patient 1 is connected via line 7 to a ventilator 8 which has a ventilation console 9.

The assembly 12 shown in FIG. 2 is used for treating patient 11, who is connected to a blood pump 14 via a cannula 13. Like cannula 3, cannula 13 is a dual lumen cannula with which blood can be withdrawn from patient 11, which blood is transported through the gas exchanger 15 by means of the blood pump 14. The blood pump 14 is controlled via the control unit 16.

The patient 11 is also connected via the line 17 to the ventilator 18, which has a ventilation console 19.

This ventilation console 19 of the ventilator 18 includes a unit 30 which is connected via the ventilator interface 31 to the control unit 16. The control unit 16 is also connected to the blood pump 14 via the pump interface 32. The unit 30 is designed to output a parameter of the breathing cycle or a parameter related to the breathing cycle, which parameter is transmitted to the control unit 16 via the ventilator interface 31 so that the control unit 16 can use this parameter to control the blood pump 14 via the blood pump interface 32.

The patient 11 is attached to a further device, an EKG 33, which is connected to the control unit 16 via an EKG interface 34. This enables it to transmit a measurement value of the impedance to the control unit 16 via the EKG interface 34 instead of or in addition to the ventilator interface 31, so that this measurement value also can be taken into account for the purpose of controlling the blood pump 14 via the blood pump interface 32. A myocardial sensor may also be used as a device instead of the EKG 33, in which case it correspondingly transmits a measurement value on the muscular activity of the diaphragm to the control unit 16 via a myocardial sensor interface.

FIG. 3 shows an assembly 22 for a patient 12 in which an evaluation unit 26 and a ventilator 28 are combined in an integrated console 35. This integrated console 35 receives measurement values via the EKG interface 34 and is connected to the patient 12 via the line 27. The interface with the ventilator 18 shown in FIG. 2 is no longer required, since the ventilator 28 is combined with the control unit 26. The integrated console 35 is thus able to control the blood pump 24 via the interface 32, the blood pump being connected to the patient 12 via the gas exchanger 25 and the cannula 23.

The console 35 is designed to derive the triggering from the predefined mechanical breathing cycle. A further device is therefore optional. Since patients in the intensive care unit are typically attached to an EKG, it is logical to use this signal as a second input.

If a patient who is ventilated by means of a tracheal tube in the windpipe wakes up from the induced coma and begins breathing spontaneously, the control unit detects a change of status and automatically changes the control of the pump or the "device input". In this case, the signal from an EKG for example can be used via a second sensor input to control the flow rate at the blood pump 14, 24.

Thus by means of the integrated console 35 a particularly simple way is provided to control the flow rate at the blood pump 24 and the gas flow at the ventilator 28, and particularly the algorithm, that is to say the "pulse" of the blood pump and the respiration cycle.

FIG. 4 shows an example of a dual lumen cannula 40 from EP19780300235 with a first fluid port 41 and a second fluid port 42. Accordingly, in operation, fluid advances through the cannula 43, which is passed through the gasket 44, until it reaches the cannula tip 45. A second fluid stream advances from the cannula area 48 via the line 46 through the radially outer coaxial cannula 47, which is retained inside the cannula barrel 49 until it reaches the cannula entry 48.

A wall of the vessel into which the cannula has been advanced can come into contact with the cannula and prevent the flow of fluid both at the cannula tip 45 and at the cannula entry 48. The area 48 of the cannula 40 where fluid particularly such as blood is aspirated is especially at risk.

When fluid is drawn out of a vessel with a simple cannula (e.g., venous femoral cannula), the cannula tip is the area which is especially susceptible.

The invention claimed is:

1. An assembly (2, 12, 22) for extracorporeal lung and heart assistance with a blood pump (4, 14, 24), a gas exchanger (5, 15, 25), a control unit (6, 16, 26) to control the flow rate at the blood pump (4, 14, 24), a cannula (3, 13, 23) to withdraw blood from a blood vessel of a patient, the cannula (3, 13, 23) being connected to the blood pump (4, 14, 24), such that blood can be transported through the gas exchanger (5, 15, 25) by means of the blood pump (4, 14, 24), and at least one device (8, 30, 33) for transmitting measurement values to the control unit (6, 16, 26), wherein the device (8, 30, 33) is designed to output a parameter of the breathing cycle or a parameter that is associated with the breathing cycle, wherein the control unit (6, 16, 26) is adapted to determine the optimum point in time for withdrawing blood from the patient depending on the patient's breathing and to adjust the blood flow accordingly to avoid or reduce adherence of the cannula (3, 13, 23) to the blood vessel wall.

2. The assembly according to claim 1, wherein the blood pump (4) includes a drive for controlling the output thereof to vary the flow rate.

3. The assembly according to claim 1, wherein the blood pump (4, 14, 24) includes a rotor for controlling the rotating speed thereof to vary the flow rate.

4. The assembly according to claim 1, wherein the device is an EKG (33) and the parameter correlates to an impedance of the EKG.

5. The assembly according to claim 1, wherein the device is a ventilator (8, 18, 28) and the parameter correlates to an inspiratory pressure of the ventilator (8, 18, 28).

6. The assembly according to claim 1, wherein the device is a chest strap and the parameter correlates to a stretching or tension in the chest strap.

7. The assembly according to claim 1, wherein the device is a piezo element.

8. The assembly according to claim 1, wherein the device is a diaphragm or myocardial sensor.

9. The assembly according to claim 1, wherein the device is a sensory gastric tube.

10. The assembly according to claim 1, wherein the control unit (6, 16, 26) monitors blood flow and gas flow parameters of a gas exchanger (5, 15, 25) and a ventilator (8, 18, 28).

11. The assembly according to claim 1, wherein the control unit (6, 16, 26) selects or combines measurement values from different devices (8, 18, 28, 33) on the basis of previously entered data to control the flow rate at the blood pump (4, 14, 24).

12. The assembly according to claim 1, wherein a buffer element is arranged after the blood pump (4, 14, 24).

13. The assembly according to claim 1, wherein the cannula is a dual lumen cannula.

14. A method comprising:
providing an assembly (2, 12, 22) for extracorporeal lung and heart assistance with a blood pump (4, 14, 24), a gas exchanger (5, 15, 25), a control unit (6, 16, 26) to control the flow rate at the blood pump (4, 14, 24), a cannula (3, 13, 23) to withdraw blood from a blood vessel of a patient, the cannula (3, 13, 23) being connected to the blood pump (4, 14, 24), such that blood can be transported through the gas exchanger (5, 15, 25) by means of the blood pump (4, 14, 24), and at least one device (8, 30, 33) for transmitting measurement values to the control unit (6, 16, 26), wherein the device (8, 30, 33) is designed to output a parameter of the breathing cycle or a parameter that is associated with the breathing cycle, wherein the control unit (6, 16, 26) is adapted to determine the optimum point in time for withdrawing blood from the patient depending on the patient's breathing and to adjust the blood flow accordingly to avoid or reduce adherence of the cannula (3, 13, 23) to the blood vessel wall; and
comparing the measurement values of or associated with the breathing cycle of the patient with predefined measurement values by the control unit (6, 16, 26) for the purpose of controlling the flow rate of the blood pump (4, 14, 24) to withdraw blood from the patient at an optimum point in time to avoid or reduce adherence of the cannula (3, 13, 23) to the blood vessel wall.

15. The method according to claim 14, wherein the measurement values are compared with predefined measurement values by the control unit (6, 16, 26) for the purpose of controlling the gas flow of a ventilator (8, 18, 28).

16. The method according to claim 14, wherein with the control unit (6, 16, 26) spontaneous breathing and ventilation are detected automatically and the flow rate of the blood pump (4, 14, 24) is controlled correspondingly.

* * * * *